United States Patent [19]

Bertleff et al.

[11] Patent Number: 5,003,102

[45] Date of Patent: Mar. 26, 1991

[54] PREPARATION OF 5-FORMYLVALERIC ESTERS

[75] Inventors: Werner Bertleff, Viernheim; Rolf Fischer, Heidelberg; Rudolf Kummer; Franz Merger, both of Frankenthal; Heinz-Walter Schneider, Ludwigshafen, all of Fed. Rep. of Germany

[73] Assignee: BASF Aktiengesellschaft, Ludwigshafen, Fed. Rep. of Germany

[21] Appl. No.: 206,751

[22] Filed: Jun. 15, 1988

[30] Foreign Application Priority Data

Jun. 15, 1987 [DE] Fed. Rep. of Germany ....... 3719933

[51] Int. Cl.$^5$ ...................... C07C 67/38; C07C 69/67
[52] U.S. Cl. .................................... 560/177; 560/210
[58] Field of Search ................................ 560/177, 210

[56] References Cited

U.S. PATENT DOCUMENTS

| | | | |
|---|---|---|---|
| 4,035,408 | 7/1977 | Smith | 560/266 |
| 4,360,692 | 11/1982 | Kummer et al. | 560/175 |
| 4,517,400 | 5/1985 | Pesa et al. | 585/638 |
| 4,537,987 | 8/1985 | Schneider et al. | 560/193 |

FOREIGN PATENT DOCUMENTS 0031100 7/1981 European Pat. Off. .
0125567 11/1984 European Pat. Off. .

*Primary Examiner*—Vivian Garner
*Attorney, Agent, or Firm*—Keil & Weinkauf

[57] ABSTRACT

5-Formylvaleric esters are prepared by a process which comprises the following steps:

(a) Hydroformylation of a pentenoic ester by reaction with carbon monoxide and hydrogen at elevated temperatures and under superatmospheric pressure in the presence of a carbonyl complex of a metal of group 8 of the Periodic Table with formation of a mixture of 5-, 4- and 3-formylvaleric esters, (b) Isolation of the 5-formylvaleric ester from the resulting mixture of 5-, 4- and 3-formylvaleric esters, a mixture essentially consisting of 4- and 3-formylvaleric esters remaining, (c) Cleavage of the mixture essentially consisting of 4- and 3-formylvaleric esters at from 50° to 400° C. in the presence of a catalyst to give pentenoic esters and (d) Recycling of the pentenoic esters to stage (a).

11 Claims, No Drawings

PREPARATION OF 5-FORMYLVALERIC ESTERS

European Patent 31,100 discloses that 5-formylvaleric esters are obtained by hydroformylation of pentenoic esters. This procedure gives a mixture of formylvaleric esters which contains 70% of the desired 5-formylvaleric esters. Attempts have also been made first to isomerize 3-pentenoic esters to 4-pentenoic esters and then to subject the latter to hydroformylation to increase the proportion of straight-chain formylvaleric esters, as described in European Patent 125,567. Apart from the fact that an additional isomerization step is expensive, substantial amounts of useless branched formylvaleric esters are still obtained.

It is an object of the present invention to provide a process for the preparation of 5-formylvaleric esters starting from pentenoic esters, in which pentenoic esters are converted as completely as possible into 5-formylvaleric esters, additional isomerization of pentenoic esters to 4-pentenoic esters is not necessary and finally the production of useless branched formylvaleric esters and further byproducts is substantially avoided.

We have found that this object is achieved by a process for the preparation of 5-formylvaleric esters which comprises the following steps:

(a) Hydroformylation of a pentenoic ester by reaction with carbon monoxide and hydrogen at elevated temperatures and under superatmospheric pressure in the presence of a carbonyl complex of a metal of group 8 of the Periodic Table with formation of a mixture of 5-, 4- and 3-formylvaleric esters, (b) Isolation of the 5-formylvaleric ester from the resulting mixture of 5-, 4- and 3-formylvaleric esters, a mixture essentially consisting of 4- and 3-formylvaleric esters remaining, (c) Cleavage of the mixture essentially consisting of 4- and 3-formylvaleric esters at from 50° to 400° C. in the presence of a catalyst to give pentenoic esters and (d) Recycling of the pentenoic esters to stage (a) for hydroformylation.

The novel process has the advantage that pentenoic esters can be converted, without prior isomerization to 4-pentenoic esters, into 5-formylvaleric esters with minimization of the amount of byproducts produced.

This was not to be expected since, according to European Patent Application 81,090, formylvaleric esters give dihydropyrones when heated at from 200° to 350° C. in the presence of a catalyst.

In stage (a), pentenoic esters are subjected to hydroformylation. Suitable pentenoic esters are derived from alkanols of 1 to 12 carbon atoms and cycloalkanols of 5 to 8 carbon atoms. $C_1$-$C_6$-alkyl pentenoates are particularly preferred, especially $C_1$-$C_4$-alkyl pentenoates, very particularly the methyl esters. 4-pentenoic esters, 3-pentenoic esters and 2-pentenoic esters are suitable, either individually or as a mixture. Examples are methyl, ethyl, propyl, isopropyl, butyl, tert-butyl, hexyl, nonyl, dodecyl, cyclopentyl and cyclohexyl 2-pentenoate, 3-pentenoate and 4-pentenoate.

The hydroformylation of the pentenoic esters is carried out in a conventional manner, for example according to European Patent 31,100, at elevated temperatures, but advantageously, in a novel variant, at from 60° to 160°, in particular from 80° to 110° C. In this procedure it is advantageous to maintain superatmospheric pressure of from 50 to 300, in particular from 90 to 150, bar. The hydroformylation of the pentenoic esters is carried out by a reaction with carbon monoxide and hydrogen. As a rule, the gas mixture contains carbon monoxide and hydrogen in a molar ratio of from 1:0.5 to 1:10, in particular from 1:1 to 1:2.

The hydroformylation is effected in the presence of a carbonyl complex of a metal of subgroup 8 of the Periodic Table. Cobalt carbonyl and rhodium carbonyl complexes are particularly suitable. Cobalt carbonyl complexes have proven particularly useful. Advantageously, from 0.01 to 1, preferably from 0.05 to 0.3, in particular from 0.08 to 0.25, mol %, calculated as cobalt and based on pentenoic esters used, of a cobalt carbonyl complex is employed. During the hydroformylation, it is advantageous to maintain a conversion of from 10 to 50%, preferably from 20 to 40%, based on the pentenoic esters used. This reduces the formation of byproducts by hydrogenation and aldolization. Under these conditions, it is possible to dispense with the presence of solvents and to use cobalt catalysts which contain up to 20 moles of tertiary nitrogen bases per mole of cobalt without adversely affecting the hydroformylation. Such catalysts are obtained, for example, in the hydroesterification of butadiene to pentenoic esters, as described in European Patent 31,100.

However, it is also possible to carry out the hydroformylation in the presence of solvents which are inert under the reaction conditions. Examples of suitable solvents are ethers, such as tetrahydrofuran, or toluene or carboxylic esters, such as valeric esters, butyric esters or acetic esters.

The hydroformylation mixture is let down and then worked up by a known method. A suitable method is described in, for example, European Patent 31,100. In this procedure, the discharged mixture from the hydroformylation is let down and then treated with an oxidizing agent, such as hydrogen peroxide or a gas containing molecular oxygen, in particular air, advantageously in an amount of from 2 to 10 oxidation equivalents per mole of cobalt compound, in the presence of an aqueous acidic solution, for example aqueous formic acid, acetic acid or higher carboxylic acids, such as butyric acid, valeric acid or 2-ethylhexanoic acid, at, for example, from 80° to 160° C., in particular from 100° to 130° C. Depending on the degree of mixing, the cobalt catalyst has separated out completely after only a few seconds or fractions of a second. The cobalt-containing aqueous phase is advantageously separated off by decanting. The organic phase obtained is a mixture of 5-, 4- and 3-formylvaleric esters which furthermore contains high boilers and valeric esters as byproducts and may contain unconverted pentenoic esters.

This organic phase is separated by fractional distillation in such a way that any solvent used and unconverted pentenoic esters are separated off individually or as a mixture and advantageously recycled to the hydroformylation stage. The 5-formylvaleric ester is isolated from the remaining mixture containing 5-, 4- and 3-formylvaleric esters by distillation, a mixture essentially consisting of 4- and 3-formylvaleric esters remaining (stage b).

In the subsequent stage (c), the resulting mixture essentially consisting of 4- and 3-formylvaleric esters is subjected to cleavage in the presence of a catalyst at from 50° to 400° C. with formation of pentenoic esters.

For the cleavage according to the invention, it is possible to use the pure 4- and 3-formylvaleric esters. In general, however, it is advantageous to use the resulting mixtures, which may also contain 5-formylvaleric esters, depending on the efficiency of the distillation. A typical mixture contains, for example, from 60 to 75% by weight of 4-formylvaleric ester, from 25 to 35% by weight of 3-formylvaleric ester and not more than 5% by weight of 5-formylvaleric ester. The cleavage products obtained are 4-, 3- and 2-pentenoic esters, predominantly 3-pentenoic esters, in addition to carbon monoxide and hydrogen.

Catalysts advantageously used in stage (c) are those which contain one or more elements of subgroup 8 of the Periodic Table and advantageously may additionally contain one or more elements of subgroups 1 to 7 and/or rare earth elements.

Advantageously used homogeneous catalysts are complexes of noble metals of subgroup 8, in particular ruthenium or rhodium. Ruthenium or rhodium complexes which contain halogens, such as chlorine or bromine, and phosphines or phosphites and may additionally contain carbon monoxide as a ligand are particularly suitable. Tertiary organic phosphines are particularly preferably used as modifiers. Preferred substituents of such phosphines are alkyl of not more than 18 carbon atoms, cycloalkyl of 5 to 12 carbon atoms, aralkyl of 7 to 10 carbon atoms or aryl of 6 to 10 carbon atoms, in particular phenyl. The radicals may be identical or different. Examples of suitable complexes are $RhCl[(P(C_6H_5)_3], Ru_2Cl_3[(P(C_6H_5)(C_2H_5)_2)_6]Cl, RhBr(CO)[P(C_6H_5)_3]_2, HRuCl(CO)[P(C_6H_5)_3]_3, RHCl(CO)[P(C_6H_5)_3]_2$.

Preferably used supported catalysts are those which contain one or more of the elements of subgroup 8 of the Periodic Table, such as palladium, platinum, ruthenium, rhodium, osmium, iridium, iron, cobalt or nickel, in particular noble metals. Other advantageous supported catalysts are those which contain two or more noble metals of subgroup 8, such as ruthenium, rhodium, palladium, platinum, iridium or osmium. Other preferred catalysts contain one or more of the abovementioned noble metals of subgroup 8 of the Periodic Table and in addition one or more metals selected from the group consisting of iron, cobalt and nickel.

The supported catalysts advantageously contain from 0.01 to 10, preferably from 0.05 to 5, in particular from 0.05 to 1, % by weight, based on the sum of the carrier and catalytically active metals and calculated as metal, of active metals of subgroup 8 of the Periodic Table. Advantageously used carriers are alumina, silica, titanium dioxide, zinc oxide, lanthanum oxide, barium sulfate, zirconium dioxide or mixtures of these oxides, as well as aluminum silicates.

The stated supported catalysts also particularly advantageously contain one or more elements of subgroups 1 to 7 and/or rare earth elements, for example zinc, copper, silver, lanthanum, titanium, vanadium, chromium, molybdenum, tungsten, manganese, rhenium, cerium, neodymium or praesodymium, advantageously in an amount of from 0.05 to 2% by weight, based on the total weight of the catalyst (carrier and catalytically active metals) and calculated as metals.

For example, impregnated catalysts in which the catalytically active metals are concentrated at the surface of the carrier have proven useful. Catalysts of this type are obtained in a conventional manner by impregnating preshaped carriers, such as pellets, spheres or extrudates, with an aqueous solution of the metal salts, for example the nitrates, and the products can then be dried, calcined and used directly or, if necessary, after reduction with hydrogen or another reducing agent.

The catalysts used in stage (c) have high activity over a prolonged period. Spent catalysts can be regenerated by treatment with an oxygen-containing gas, for example air, at from 350° to 500° C., followed by reduction.

During the cleavage of the formylvaleric esters in stage (c), a temperature of from 50° to 400° C., preferably from 60° to 350° C., in particular from 100° to 280° C., particularly advantageously from 120° to 200° C., is maintained. In general, the cleavage is carried out under atmospheric pressure, but it is also possible to use reduced or superatmospheric pressure, advantageously from 10 mbar to 20 bar. In general, a space velocity of from 0.01 to 40, preferably from 0.1 to 20, kg of formylvaleric ester per kg of catalyst per hour is maintained.

It may be advantageous to carry out the cleavage of the formylvaleric esters in stage (c) in the presence of a diluent. Examples of suitable diluents are water, alcohols, such as methanol, ethanol, butanol or cyclohexanol, ethers, such as dioxane or tetrahydrofuran, chlorohydrocarbons, such as methylene chloride, chloroform or 1,2-dichloromethane, aliphatic, cycloaliphatic or aromatic hydrocarbons, such as benzene, toluene, cyclohexane or paraffins, and esters, such as acetates or propionates.

It is advantageous to use the alcohol which corresponds to the alcohol of the formylvaleric esters. Thus, the educt and product have sufficiently different boiling points and can therefore readily be separated by distillation. It has proven useful if the molar ratio of formylvaleric esters to diluents is from 1:0.1 to 1:50, in particular from 1:0.5 to 1:20. Particularly preferred diluents are water and alkanols of 1 to 6 carbon atoms, in particular methanol.

The cleavage in stage (c) is advantageously carried out in the presence of molecular oxygen or a gas which contains molecular oxygen and an inert gas, such as nitrogen, carbon dioxide, argon or steam. A molar ratio of formylvaleric esters to molecular oxygen of from 1:0.05 to 1:3, in particular from 1:0.2 to 1:1.5, e.g., from 1:0.25 to 1:1.25, is advantageously used. This increases the catalyst life and in particular the yield of pentenoic esters. The presence of molecular oxygen was not indicated since methyl 5-formylvalerate is oxidized to monomethyl adipate in a yield of 96% by molecular oxygen at as low as 50° C., as disclosed in European Patent 131,860, and it was therefore to be expected that 4- and 3-formylvaleric esters would be oxidized in a similar manner to give 2-methylglutaric acid and 3-ethylsuccinic esters.

The reaction in stage (c) may be carried out batchwise or continuously as a fixed-bed reaction using a fixed-bed catalyst, for example by a liquid phase or trickle-bed method in the liquid or gas phase, or as a fluidized-bed reaction with the catalyst fluidized upward and downward, in the gas phase or in the liquid phase with soluble catalysts or suspended supported catalysts.

In a preferred embodiment of stage (c) in the liquid phase, for example, the formylvaleric ester and, if required, the diluent, together with the oxygen-containing gas, are passed over a solid catalyst at below the boiling point of the formylvaleric ester, or are heated in the presence of a suspended solid catalyst or of a dissolved homogeneous catalyst. After the catalyst has been removed, the liquid reaction product is then separated into the pentenoic ester and, where relevant, diluent and unconverted formylvaleric ester by distillation.

In a preferred embodiment of stage (c) of the novel process in the gas phase, for example, a mixture of formylvaleric ester and, if required, diluent is vaporized and then passed, together with air and advantageously also a carrier gas, such as nitrogen, carbon dioxide or argon, in gaseous form, at the abovementioned temperature, into a fixed-bed or fluidized-bed catalyst. The reacted mixture is condensed and then separated by fractional distillation. Unconverted formylvaleric esters are advantageously recycled to stage (c). The resulting mixture of 4-, 3- and 2-pentenoic esters is recycled to the hydroformylation stage (a), if necessary with pentenoic esters obtained in stage (b), for the preparation of 5-formylvaleric esters. The valeric esters obtained as byproducts can be separated off or likewise recycled as solvents to stage (a).

In the novel process, it is possible to convert pentenoic esters into 5-formylvaleric esters in high yield by hydroformylation since the isomeric formylvaleric esters obtained as byproducts are recycled to the hydroformylation after cleavage to give pentenoic esters.

5-Formylvaleric esters obtainable by the process of the invention are suitable, for example, for the preparation of aminocaproic esters. The Examples which follow illustrate the process according to the invention.

EXAMPLES 1 TO 8

Stage (a)

The hydroformylation experiments were carried out by a continuous procedure. The apparatus had a liquid metering pump, by means of which the methyl pentenoate nd the dissolved cobalt catalyst were conveyed into the two stirred autoclaves connected in series. The synthesis gas was combined with the liquid feed upstream of the first reactor, the pressure being regulated. The two reactors had liquid volumes of 1.2 and 1.12 l, respectively. The two-phase mixture discharged was collected under superatmospheric pressure in a container, from which a certain amount of waste gas was discharged through a regulating valve. The liquid phase was let down into a receiver, the level being regulated. In Examples 1 and 2, the stated amount of $Co_2(CO)_8$ was used as the catalyst and a synthesis gas comprising 1:1 $CO/H_2$ was employed.

Examples 1-3 describe the effect of the cobalt concentration on conversion, proportion of straight-chain compounds in the aldehyde mixture and formation of high boilers.

Examples 4 and 5 describe the effect of temperature, at constant cobalt concentration, on conversion, proportion of straight-chain compounds and formation of high boilers.

Examples 6-8 describe the effect of pressure on conversion, proportion of straight-chain compounds and formation of high boilers.

Further details are shown in Table 1.

TABLE 1

Results of the hydroformylation on methyl 3-pentenoate (PSE)
Feed: methyl 3-pentenoate with the appropriate amount of dissolved $Co_2(CO)_8$
Space velocity $0.15 \text{ L} \times 1^{-1} \times h^{-1}$

| Example | $\frac{\text{Moles of Co}}{\text{Moles of PSE}} \times 100 \, [\%]$ | Pressure/ bar | Temp./ °C. | % Conversion | % n content[1] | % (m/m) of high boilers in discharge | Percent selectivity of valeric ester | Percent selectivity of FVSE[4] |
|---|---|---|---|---|---|---|---|---|
| 1 (comparison) | 2 | 200 | 110 | 97.7 | 55 | 52[2] | 5.6 | 42.3 |
| 2 | 0.48 | 200 | 110 | 86.6 | 59.6 | 37[2] | 2.9 | 60.1 |
| 3 | 0.16 | 200 | 110 | 69.7 | 68.0 | 14.6[2] | 2.1 | 83.2 |
| 4 | 0.16 | 200 | 100 | 37.2 | 69.5 | 3.5[2] | 0.8 | 94.4 |
| 5 | 0.16 | 200 | 90 | 17.6 | 69 | 0.3[3] | 1.7 | 97.4 |
| 6 | 0.16 | 280 | 100 | 39.5 | 69.1 | 8.8[2] | 1.9 | 89.0 |
| 7 | 0.16 | 130 | 100 | 33.2 | 69.4 | 1.7[3] | 1.6 | 96.5 |
| 8 | 0.16 | 90 | 100 | 32.8 | 68.7 | <0.3[3] | 0.9 | 98.8 |

[1]Content of methyl 5-formylvalerate in the total amount of methyl formylvalerates
[2]Determination by GC (internal standard method)
[3]Determination by distillation
[4]Sum of all isomeric formylvalerates (FVSE)

EXAMPLE 9

Stage (a)

In the same apparatus as in Example 2, methyl 3-pentenoate was converted with 0.16 mol % of cobalt using a space velocity of 0.3 instead of 0.15 $1 \times 1^{-1} \times h^{-1}$ at 100° C. and 200 bar $CO/H_2$. At a conversion of 15.5%, the total selectivity with respect to formylvaleric esters was 98.7% and the proportion of straight-chain compounds was 70.5%. 1.2% of the pentenoic ester converted were hydrogenated to valeric ester.

EXAMPLE 10

(Variation of the synthesis gas composition)
Stage (a)

The procedure described in Example 7 was followed, except that the $CO/H_2$ ratio was 6:4 instead of 1:1. A conversion of 19.8% and a total selectivity with respect to formylvaleric esters of 99.2% were achieved, the proportion of straight-chain compounds being 68.9%. 0.8% of the pentenoic ester converted was hydrogenated to valeric ester.

EXAMPLE 11

(Effect of N bases on catalyst activity)
Stage (a)

Instead of $Co_2(CO)_8$, a catalyst solution from a preceding hydroesterification of butadiene to methyl pentenoate was used. After pentenoates and low boilers had been distilled off, some of the bottom product was used as a catalyst for the hydroformylation. This bottom product contained 2.2 moles of pyridine, based on cobalt. Methyl pentenoate was hydroformylated using this catalyst (0.16 mol % of Co) similarly to Example 7, under 130 bar and at 100° C. At a conversion of 33%, methyl formylvalerate was obtained with a selectivity of 97% and a proportion of straight-chain compounds of 68%; about 2% of the pentenoic ester converted was hydrogenated to valeric ester.

EXAMPLE 12

Stage (a)

A mixture of methyl 3-pentenoate was hydroformylated similarly to Example 7 using 800 ppm of cobalt in the form of $Co_2(CO)_8$ (360 ml/h) at 100° C. and under 130 bar (1:1 $CO/H_2$). 327 g/h were discharged, the discharged mixture having the following composition:
38.1% (m/m) of formylvaleric ester (containing 69.6% of n components)
0.4% (m/m) of methyl valerate
61.2% (m/m) of methyl pentenoate.

This result corresponds to a conversion of 33%, a selectivity of 98.8% for all formylvaleric esters and a selectivity of 68.8% for 5-formylvaleric ester.

This discharged mixture was passed together with 150 ml/hour of 5% strength acetic acid through a tube, 5 l/h of air being passed in and thorough mixing effected. After phase separation, 154 ml of a 0.2% strength cobalt acetate solution (calculated as cobalt) were separated off.

In a batchwise distillation, 835 g of the organic phase were separated into about 3 g of methyl valerate, 495 g of methyl 3-pentenoate, 12 g of methyl 2-transpentenoate and about 315 g of a mixture of methyl 5-, 4- and 3-formylvalerate, and 6 g of residue.

Stage (b)

The mixture of methyl formylvalerates was separated into 215 g of 99% pure methyl 5-formylvalerate, 90 g of a mixture of methyl 5-, 4- and 3-formylvalerates (2% of 5-, 70% of 4- and 28% of 3-FVSE) and 10 g of residue by further fractional distillation.

Stage (c)

90 g of the mixture of methyl 5-, 4- and 3-formylvalerate together with 180 g of methanol were pumped into an evaporator in the course of 1 hour and passed from there, together with 70 l of air at 250° C. over 200 g of an $SiO_2$ supported catalyst which contained 0.5% of Ru, 0.5% of Rh and 0.5% of Pt. When the condensed reacted mixtures (260 g) were worked up by distillation, 15% of methyl 4-pentenoate, 53% of methyl 3-pentenoate and 15% of methyl 2-trans-pentenoate and 17% of methyl valerate were obtained after removal of methanol and water. In addition, 10 g of a mixture of methyl 4- and 3-formylvalerate were recovered.

Stage (d)

The mixture of methyl 4-, 3- and 2-pentenoate was recycled to stage a and, even in the presence of the methyl valerate, could be reused for the hydroformylation with virtually the same yield as that obtained starting from methyl 3-pentenoate.

EXAMPLES 13–15

Stage (c)

30 ml/h of a methyl formylvalerate mixture (35% of 3-FVSE and 57% of 4-FVSE) which had been obtained according to Example 8 and by subsequent fractional distillation of the reacted mixture were passed, together with 30 l/h of carrier gas of the stated composition, over 20 g of a fixed-bed catalyst. The gaseous reaction products were condensed, and analyzed by gas chromatography.

| No. | Catalyst | $N_2$/air [l/h] | PSE [% by wt.] | Conversion [%] | Selectivity [%] |
|---|---|---|---|---|---|
| 13 | 0.75% Pd + 0.1% V on $SiO_2$ | 24/6 | 47.4 | 81 | 62 |
| 14 | 0.75% Pd + 0.04% Co on $SiO_2$ | 18/12 | 69.7 | 87 | 84 |
| 15 | 0.75% Pd + 0.06% Mn on $SiO_2$ | 18/12 | 74.7 | 91 | 83 |

We claim:

1. A process for the preparation of a 5-formylvaleric ester which comprises the following steps:
   (a) hydroformylation of a pentenoic ester by reaction with carbon monoxide and hydrogen at elevated temperatures and under superatmospheric pressure in the presence of a carbonyl complex of a metal of group 8 of the Periodic Table with formation of a mixture of 5-, 4- and 3-formylvaleric esters,
   (b) isolation of the 5-formylvaleric ester from the resulting mixture of 5-, 4- and 3-formylvaleric esters, a mixture essentially consisting of 4- and 3-formylvaleric esters remaining,
   (c) cleavage of the mixture essentially consisting of 4-and 3-formylvaleric esters at from 50° to 400° C. in the presence of a catalyst comprising one or more elements of subgroup 8 of the Periodic Table and optionally, one or more elements selected from the group consisting of copper, silver, zinc, titanium vanadium, chromium, molybdenum, tungsten, manganese and rhodium, and optionally, in the presence of molecular oxygen or a gas containing molecular oxygen and optionally, in the presence of a diluent to give pentenoic esters and
   (d) recycling of the pentenoic esters to stage (a) for hydroformylation.

2. The process of claim 1, wherein, in stage (a), a cobalt concentration of from 0.05 to 0.3 mol %, based on the pentenoic ester, is maintained.

3. The process of claim 1, wherein, in stage (a), a conversion of pentenoate of from 10 to 50% is maintained.

4. The process of claim 1, wherein, in stage (a), a temperature of from 60° to 160° C. is maintained.

5. The process of claim 1, wherein in stage (c), a supported catalyst is used contains two or more noble metals of subgroup 8 of the Periodic Table.

6. The process of claim 1, wherein in stage (c), a supported catalyst is used contains one or more noble metals of subgroup 8 of the Periodic Table and one or more metals selected from the group consisting of iron, cobalt and nickel.

7. The process of claim 1, wherein the reaction in stage c is carried out at from 60° to 350° C.

8. The process as claimed in claim 1, wherein the cleavage in stage (c) is carried out with the addition of molecular oxygen or of a gas containing molecular oxygen.

9. The process of claim 8 wherein a molar ratio of formylvaleric ester to molecular oxygen of from 1:0.05 to 1:3 is maintained.

10. The process of claim 1, wherein a diluent is present in stage (c).

11. The process of claim 1, wherein the reaction in stage c is carried out in the presence of water or an alkanol of 1 to 6 carbon atoms or a mixture of thereof as diluent.

* * * * *